(12) United States Patent
Gross et al.

(10) Patent No.: US 8,617,126 B2
(45) Date of Patent: Dec. 31, 2013

(54) PAINLESS INJECTOR

(75) Inventors: Yossi Gross, Moshav Mazor (IL); Oz Cabiri, Macabim-Reut (IL)

(73) Assignee: MEDIMOP Medical Projects Ltd., Ra'anana (IL)

( * ) Notice: Subject to any disclaimer, the term of this patent is extended or adjusted under 35 U.S.C. 154(b) by 132 days.

(21) Appl. No.: 13/063,236

(22) PCT Filed: Sep. 14, 2009

(86) PCT No.: PCT/US2009/056778
§ 371 (c)(1),
(2), (4) Date: Mar. 10, 2011

(87) PCT Pub. No.: WO2010/030965
PCT Pub. Date: Mar. 18, 2010

(65) Prior Publication Data
US 2011/0166509 A1     Jul. 7, 2011

Related U.S. Application Data

(60) Provisional application No. 61/192,198, filed on Sep. 15, 2008.

(51) Int. Cl.
*A61M 5/00* (2006.01)
*A61M 5/32* (2006.01)
*A61M 5/31* (2006.01)

(52) U.S. Cl.
USPC ............ 604/239; 604/117; 604/181; 604/272

(58) Field of Classification Search
USPC ............... 604/60, 239–243, 46–47, 115–117, 604/181, 272
See application file for complete search history.

(56) References Cited

U.S. PATENT DOCUMENTS

| | | | |
|---|---|---|---|
| 4,195,636 A | 4/1980 | Behnke | |
| 4,222,380 A * | 9/1980 | Terayama | ...................... 604/115 |
| 4,403,987 A | 9/1983 | Gottinger | |
| 5,190,521 A | 3/1993 | Hubbard et al. | |
| 5,478,315 A | 12/1995 | Brothers et al. | |
| 5,662,678 A | 9/1997 | Macklin | |
| 5,766,186 A | 6/1998 | Faraz et al. | |
| 6,200,296 B1 | 3/2001 | Dibiasi et al. | |
| 6,743,211 B1 | 6/2004 | Prausnitz et al. | |

(Continued)

FOREIGN PATENT DOCUMENTS

| | | |
|---|---|---|
| EP | 0 526 986 A1 | 2/1993 |
| WO | 2006/016364 A2 | 2/2006 |
| WO | 2006/069380 A1 | 6/2006 |

OTHER PUBLICATIONS

Int'l Search Report issued on Aug. 11, 2010 in Int'l Application No. PCT/US2009/056778.

*Primary Examiner* — Nicholas Lucchesi
*Assistant Examiner* — Rebecca E Eisenberg
(74) *Attorney, Agent, or Firm* — Panitch Schwarze Belisario & Nadel LLP

(57) ABSTRACT

Apparatus for use with tissue (22) of a subject, including a substance (24) configured to be injected into the tissue, and first and second tissue-squeezing surfaces (20) configured to be placed on first and second sides of the tissue, to exert pressure on the tissue by being moved toward each other in response to a squeezing force (F), and to facilitate injection of the substance into the tissue by releasing the substance in response to application of the squeezing force.

15 Claims, 18 Drawing Sheets

(56) References Cited

U.S. PATENT DOCUMENTS

| | | |
|---|---|---|
| 7,060,054 B2 | 6/2006 | Nissels |
| 7,291,159 B2 | 11/2007 | Schmelzeisen-Redeker et al. |
| 7,740,600 B2 | 6/2010 | Slatkine et al. |
| 2004/0030353 A1 | 2/2004 | Schmelzeisen-Redeker et al. |
| 2005/0033234 A1 | 2/2005 | Sadowski et al. |
| 2006/0293722 A1 | 12/2006 | Slatkine et al. |
| 2007/0270745 A1* | 11/2007 | Nezhat et al. .......... 604/115 |
| 2009/0043245 A1 | 2/2009 | Nguyen |
| 2009/0118662 A1* | 5/2009 | Schnall .................. 604/20 |

* cited by examiner

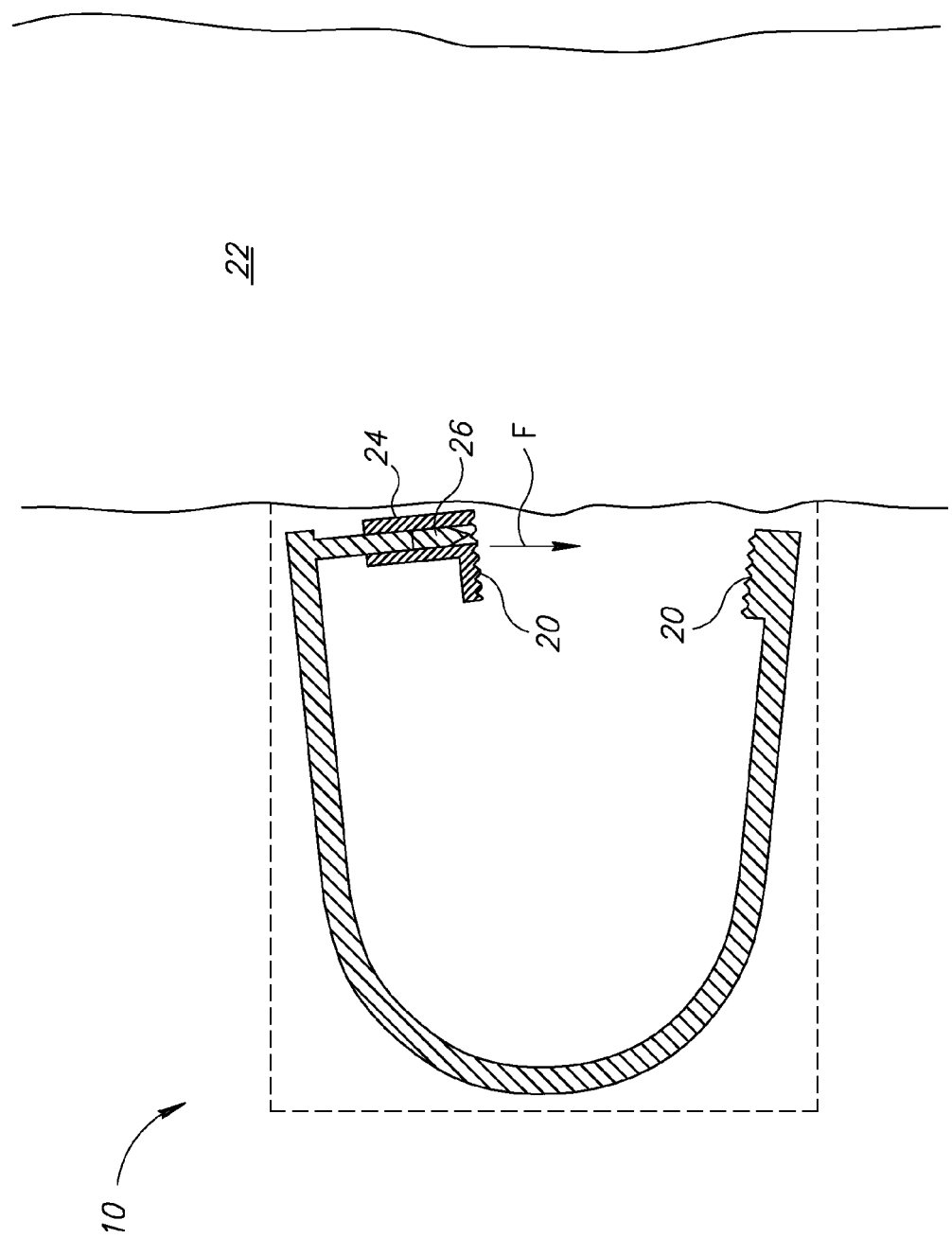

PAINLESS INJECTOR

CROSS-REFERENCE TO RELATED APPLICATION

This application is a Section 371 of International Application No. PCT/US2009/056778, filed Sep. 14, 2009, which was published in the English language on Mar. 18, 2010, under International Publication No. WO 2010/030965 A1, and the disclosure of which is incorporated herein by reference.

FIELD OF THE INVENTION

The present invention generally relates to medical apparatus. Specifically, the present invention relates to injecting substances into a subject's body in a painless manner.

BACKGROUND OF THE INVENTION

Drugs are commonly administered to patients via injections. Many patients associate injections with pain. A number of different methods are used to reduce the pain associated with an injection, for example, applying a topical anesthetic and/or ice to the injection site before the injection procedure.

U.S. Pat. No. 6,743,211 to Prausnitz at al., relevant portions of which are incorporated herein by reference, describes microneedle devices and methods of use thereof for the transport of molecules, including drugs and biological molecules, across tissue by improving the interaction of microneedles and a deformable, elastic biological barrier, such as human skin. The devices and methods are described as acting to (1) limit the elasticity, (2) adapt to the elasticity, (3) utilize alternate ways of creating the holes for the microneedles to penetrate the biological barrier, other than the simply direct pressure of the microneedle substrate to the barrier surface, or (4) any combination of these methods. Embodiments are described for limiting the elasticity of skin. The microneedle device includes features suitable for stretching, pulling, or pinching the skin to present a more rigid, less deformable, surface in the area to which the microneedles are applied (i.e. penetrate). Embodiments are described for adapting the device to the elasticity of skin, the device comprising one or more extensions interposed between the substrate and the base end of at least a portion of the microneedles.

An embodiment of the '211 patent is described in which the microneedle device includes jaws, typically one or more pairs, which can be pressed against the skin surface and triggered to close against a segment of skin. The size of the jaw opening is described as being selected based on the area of skin to be pinched to facilitate penetration of the microneedle array selected for use.

U.S. Pat. No. 5,478,315 to Brothers at al., relevant portions of which are incorporated herein by reference, describes a local anesthetic injection system for use with smaller children for providing an essentially pain free injection of a local anesthetic into a child's epidermis skin layer, above nerve endings, to deaden that skin area to receive en injection of a medicine through that deadened area utilizing a conventional hypodermic needle. The several embodiments of the system are described as including a body that has a cup arrangement with a flat edge upstanding well and is open thereacross. The cup is arranged to receive a force applied to the top thereof to urge the cup flat edge into the surface of a section of skin whereon the cup rests, causing the skin within the cup to be formed into a dome shape. A small hollow needle is maintained within the cup such that an open bevel needle end extends at an angle just below the plane of the cup edge. Thereby, as the dome of skin is formed within the cup, the needle bevel end is described as tending to travel into the dome of skin, above the skin nerve endings, allowing a vessel connecting to the needle to dispense a local anesthetic through the hollow needle bevel end when an operator applies a pressure generating force thereto.

U.S. Pat. No. 4,403,987 to Gottinger, relevant portions of which are incorporated herein by reference, describes an injection aid for supporting a hypodermic syringe and for facilitating injection of the needle of the syringe into a limb. The apparatus includes a syringe supporting member and a pair of guide rods for supporting the syringe supporting member for slideable movement between a first position wherein a needle supported by the syringe supporting member is retracted from the limb and an injecting position. A pair of spaced apart generally parallel support rods are also provided. The rearward ends of the support rods are adapted to rest on the limb and are integrally joined to the guide rods and are for supporting the guide rods. The support rods include forward ends for pinching flesh therebetween to cause the flesh adjacent the syringe needle to pucker.

U.S. Pat. No. 7,291,159 to Schmelzeisen-Redeker, relevant portions of which are incorporated herein by reference, describes a system for withdrawing body fluid from a body part in particular the finger pad, comprising a compression unit that is deformed when the body part is pressed against it and increases the internal pressure in a region of the body part, and a withdrawal device. Deformation of the compression unit is described as partially converting the primary pressing movement into a secondary movement which leads to an increase in the internal pressure in a region of the body part. A system for stimulating the outflow of body fluid using a deformable compression unit is also described.

US Patent Application Publication 2006/0293722 to Slatkine, relevant portions of which are incorporated herein by reference, describes apparatus adapted to inhibit pain signals generated by pain receptors in the skin during a skin related medical treatment such as an injection. An evacuation chamber is provided with an essentially rigid interface element larger than a threshold surface area through which a medical treatment can be administered to a selected skin region, one or more walls which are placeable in the vicinity of the skin region, an interior defined by the walls and by the interface element, and an opening at the bottom of the interior which is sealable by the skin region. A device is described as generating a vacuum within the evacuation chamber interior to a level greater than the threshold vacuum level suitable for drawing the skin region through the opening towards, and in a compressing relation against, the interface element, to inhibit the transmission of a pain signal generated by pain receptors located within the skin region.

The following patents and patent applications, relevant portions of which are incorporated herein by reference, may be of interest:

PCT Publication WO 06/069380 to Nguyen
U.S. Pat. No. 5,766,186 to Faraz
U.S. Pat. No. 5,662,678 to Macklin
U.S. Pat. No. 4,195,636 to Behnke
U.S. Pat. No. 6,200,296 to Dibiasi et al.,
US Patent Application Publication 2005/0033234 to Sadowski et al.
U.S. Pat. No. 5,190,521 to Hubbard et al.
U.S. Pat. No. 7,060,054 to Nissels

SUMMARY OF THE INVENTION

In some embodiments of the invention, first and second tissue-squeezing surfaces are placed on first and second sides of a subject's tissue, for example, the subject's skin, or internal tissue of the subject, such as gastrointestinal tract tissue. A substance, for example, a pharmaceutical, is injected into the tissue by moving the tissue-squeezing surfaces together with a squeezing force so as to exert pressure on the tissue.

In some embodiments, microneedles on the tissue-squeezing surfaces are pushed together with the squeezing force, causing the microneedles to penetrate the tissue. In some embodiments, pushing the tissue-squeezing surfaces together causes the substance to move from a first site that is not between the squeezing surfaces to a second site that is between the squeezing surfaces. For example, squeezing the surfaces together may cause a solid mess of the substance to be moved to a position between the squeezing surfaces. The solid mass is shaped to penetrate the tissue when it is moved to between the squeezing surfaces.

In some embodiments of the invention, a substance is injected into a subject's tissue according to the following procedure. Pinching surfaces are placed on the subject's tissue, the pinching surfaces being disposed distal to a distal tip of a syringe needle. The pinching surfaces pinch a fold of tissue toward the distal tip of the syringe needle until the distal tip of the syringe needle penetrates the fold of skin. Subsequently, the substance is injected into the subject's tissue from the syringe.

In some embodiments of the invention, a pinching device is coupled to the outer surface of a syringe. A distal portion of the pinching device is placed on a subject's tissue, the distal portion of the pinching device having pinching surfaces that are disposed distal to the distal tip of the syringe needle. A fold of tissue is raised by pinching the subject's tissue with the pinching surfaces. In some embodiments, the squeezing surfaces exert a pinching pressure of at least 200 g/cm2 to 2000 g/cm2 on the subject's tissue. Typically, the pinching surfaces, by exerting the pinching pressure en the subject's tissue, reduce pain associated with the penetration of the tissue by the distal tip of the needle. Subsequent to the fold of tissue being pinched, the fold of tissue is penetrated by the distal tip of the syringe needle.

In some embodiments of the invention, a substance is injected into a subject's tissue according to the following procedure. The distal tip of a pinching device is placed on a subject's skin, the distal portion of the pinching device having two or more pinching surfaces. A syringe having a syringe needle is advanced distally through the pinching device. The pinching device is configured such that the distal advancement of the syringe through the pinching device causes the pinching surfaces to raise a fold of tissue by pinching the tissue. Typically, the pinching surfaces, by exerting the pinching pressure on the subject's tissue, are configured to reduce pain associated with the penetration of the tissue by the distal tip of the needle. Subsequent to the fold of tissue being pinched, the fold of tissue is penetrated by the distal tip of the syringe needle.

There is therefore provided, in accordance with an embodiment of the present invention, apparatus for use with tissue of a subject, including:

a substance configured to be injected into the tissue; and
first and second tissue-squeezing surfaces configured to be placed on first and second sides of the tissue, to exert pressure on the tissue by being moved toward each other in response to a squeezing force, and to facilitate injection of the substance into the tissue by releasing the substance in response to application of the squeezing force.

In an embodiment, the tissue includes skin of the subject, and the tissue-squeezing surfaces include skin-squeezing surfaces configured to exert pressure on the subject's skin by being moved toward each other in response to a squeezing force.

In an embodiment, the tissue includes internal tissue of the subject, and the tissue-squeezing surfaces include tissue-squeezing surfaces configured to contact the internal tissue and exert pressure on the subject's internal tissue by being moved toward each other in response to a squeezing force.

In an embodiment, at least one of the tissue-squeezing surfaces includes an array of microneedles, the microneedles being configured to exert pressure on the tissue and to penetrate the tissue in response to the application of the squeezing force.

In an embodiment, the substance is disposed on a surface of the microneedles.

In an embodiment, the apparatus further includes a substance reservoir, en the squeezing force is not applied, the substance is disposed within the substance reservoir, and the substance is configured to be injected into the tissue from the reservoir via the microneedles, in response to the application of the squeezing force.

In an embodiment, when the squeezing force is not applied, the substance is disposed at a first site that is not between the squeezing surfaces, and the apparatus is configured to convey the substance from the first site to a second site that is between the squeezing surfaces, in response to the application of the squeezing force.

In an embodiment, the apparatus further includes a syringe and a needle coupled thereto, disposed at the first site when the squeezing force is not applied, the substance is disposed within the syringe, and the needle is configured to penetrate the tissue and release the substance into the tissue in response to the application of the squeezing force.

In an embodiment, the apparatus is configured to rapidly convey the substance to the second site in response to the squeezing force exceeding a threshold.

In an embodiment, the threshold force is defined as a force generated between one of the squeezing surfaces and the tissue, and the apparatus is configured such that the threshold force is applied at a contact pressure of at least 500 g/cm2.

In an embodiment, the substance includes a solid mass, and the solid mass is shaped to penetrate the tissue in response to the application of the squeezing force.

In an embodiment, the apparatus is configured:
to hold the solid mass at the first site when the squeezing force is not applied, and
to decouple the solid mass from at least one of the squeezing surfaces after injection of the solid mass into the tissue.

There is further provided, in accordance with an embodiment of the present invention, apparatus for use with a syringe that has a syringe needle, the apparatus including:
pinching surfaces configured:
to be disposed distal to a distal tip of the syringe needle, and
to facilitate penetration of tissue of a subject by the distal tip of the syringe needle, by pinching a fold of tissue toward the distal tip of the syringe needle until the distal tip of the syringe needle is disposed within the fold of tissue; and
one or more operating elements configured to operate the pinching surfaces.

In an embodiment, the tissue includes skin of the subject, and the pinching surfaces are configured to facilitate penetration of the subject's skin by the distal tip of the syringe needle.

In an embodiment, the tissue includes internal tissue of the subject, and the pinching surfaces are configured to contact the subject's internal tissue and facilitate penetration of the subject's internal tissue by the distal tip of the syringe needle.

In an embodiment, the pinching surfaces are configured to pinch the fold of tissue using a pinching pressure of at least 200 g/cm2.

In an embodiment, the pinching surfaces are configured to pinch the fold of tissue using a pinching pressure of 200 g/cm2 to 2000 g/cm2.

There is additionally provided, in accordance with an embodiment of the present invention, apparatus including:
- a syringe that includes:
- a syringe needle;
- pinching surfaces:
  - disposed distal to a distal tip of the syringe needle, and
  - configured to facilitate penetration of tissue of a subject by the distal tip of the syringe needle, by pinching a fold of tissue toward the distal tip of the syringe needle until the distal tip of the syringe needle is disposed within the fold of tissue; and
- one or more operating elements configured to operate the pinching surfaces.

There is further provided, in accordance with an embodiment of the present invention, apparatus for use with a syringe having a syringe needle, the apparatus including:
- a pinching device, a proximal portion of which is shaped to define a lumen and to engage an outer surface of the syringe, a distal portion of the pinching device including first and second pinching surfaces, the pinching surfaces being configured:
  - to be disposed distal to a distal tip of the syringe needle, and
  - to facilitate penetration of tissue of a subject by the distal tip of the syringe needle, by pinching a fold of tissue toward the distal tip of the syringe needle using a pinching pressure of at least 200 g/cm2.

In an embodiment, the pinching surfaces are configured to pinch the fold of tissue using a pinching pressure of 200 g/cm2 to 2000 g/cm2.

In an embodiment, the pinching surfaces are configured to reduce pain associated with the penetration of the tissue by the distal tip of the needle, by pinching the fold of tissue.

In an embodiment, the tissue includes skin of the subject, and the pinching surfaces are configured to facilitate penetration of the subject's skin by the distal tip of the syringe needle.

In an embodiment, the tissue includes internal tissue of the subject, and the pinching surfaces are configured to contact the subject's internal tissue and facilitate penetration of the subject's internal tissue by the distal tip of the syringe needle.

There is additionally provided, in accordance with an embodiment of the present invention, apparatus including:
- a syringe that includes:
- a syringe needle; and
- a pinching device, a proximal portion of which is shaped to define a lumen and engages an outer surface of a proximal portion of the syringe, a distal portion of the pinching device including first and second pinching surfaces, the pinching surfaces being configured:
  - to be disposed distal to a distal tip of the syringe needle, and
  - to facilitate penetration of tissue of a subject by the distal tip of the syringe needle, by pinching a fold of tissue toward the distal tip of the syringe needle using a pinching pressure of at least 200 g/cm2.

There is additionally provided, in accordance with an embodiment of the present invention, apparatus for use with a syringe having a syringe needle, the apparatus including:
- a pinching device configured to be coupled to the syringe, a distal portion of the pinching device including two or more pinching surfaces, the pinching surfaces being configured:
  - in response to the syringe being advanced distally through the pinching device,
  - to facilitate penetration of tissue of a subject by a distal tip of the syringe needle, by pinching a fold of tissue toward the distal tip of the syringe needle.

In an embodiment,
the pinching device is shaped to define a contact surface which is contacted by syringe the during the distal advancement of the syringe through the pinching device, and
the apparatus further includes a helical portion coupled between the contact surface and the pinching surfaces.

In an embodiment, the pinching surfaces are configured to reduce pain associated with the penetration of the tissue by the distal tip of the needle, by pinching the fold of tissue.

In an embodiment, the tissue includes skin of the subject, and the pinching surfaces are configured to facilitate penetration of the subject's skin by the distal tip of the syringe needle.

In an embodiment, the tissue includes internal tissue of the subject, and the pinching surfaces are configured to contact the subject's internal tissue and facilitate penetration of the subject's internal tissue by the distal tip of the syringe needle.

In an embodiment, the pinching surfaces are configured to pinch the fold of tissue using a pinching pressure of at least 200 g/cm2, in response to the syringe being advanced distally through the pinching device.

In an embodiment, the pinching surfaces are configured to pinch the fold of tissue using a pinching pressure of 200 g/cm2 to 2000 g/cm2.

There is further provided, in accordance with an embodiment of the present invention, apparatus including:
- a syringe that includes:
- a syringe needle; and
- a pinching device coupled to a proximal portion of the syringe, a distal portion of the pinching device including two or more helical portions, the helical portions being configured;
  - in response to the syringe being advanced distally through the pinching device,
  - to facilitate penetration of tissue of a subject by a distal tip of the syringe needle, by pinching a fold of tissue toward the distal tip of the syringe needle.

There is additionally provided, in accordance with an embodiment of the present invention, a method for injecting a substance into tissue of a subject, including:
placing first and second tissue-squeezing surfaces on first and second sides of the tissue; and
injecting the substance into the tissue by exerting pressure on the tissue by moving the tissue-squeezing surfaces toward each other with a squeezing force.

There is further provided, in accordance with an embodiment of the present invention, a method for injecting a substance from within a syringe having a syringe needle, into tissue of a subject, the method including:
placing pinching surfaces on the tissue, the pinching surfaces being disposed distal to a distal tip of the syringe needle; and
facilitating penetration of the subject's tissue by the distal tip of the syringe needle, by pinching, with the pinching surfaces, a fold of tissue toward the distal tip of the syringe needle until the distal tip of the syringe needle is disposed within the fold of tissue.

There is additionally provided, in accordance with an embodiment of the present invention, a method for injecting a substance from within a syringe having a syringe needle, into tissue of a subject, the method including:

coupling a proximal portion of a pinching device to an outer surface of the syringe, the proximal portion of the pinching device being shaped to define a lumen;

placing a distal portion of the pinching device on the tissue, the distal portion of the pinching device being shaped to define pinching surfaces that are disposed distal to a distal tip of the syringe needle;

raising a fold of tissue by pinching the subject's tissue with the pinching surfaces; and penetrating the fold of tissue with the distal tip of the syringe needle.

There is further provided, in accordance with an embodiment of the present invention, a method for injecting a substance from within a syringe having a syringe needle, into tissue of a subject, the method including:

placing a distal portion of a pinching device on the tissue, the distal portion of the pinching device defining pinching surfaces that are disposed distal to a distal tip of the syringe needle;

raising a fold of tissue by pinching the subject's tissue with the pinching surfaces with a pinching pressure of at least 200 g/cm2; and penetrating the fold of tissue with the distal tip of the syringe needle.

In an embodiment, pinching the subject's tissue with the pinching surfaces includes reducing pain associated with the penetration of the tissue by the distal tip of the needle.

In an embodiment, placing the distal portion of the pinching device on the tissue includes placing the distal portion of the pinching device on the tissue when a lumen defined by a proximal portion of the pinching device is in engagement with an outer surface of the syringe.

There is additionally provided, in accordance with an embodiment of the present invention, a method for injecting a substance from within a syringe having a syringe needle, into tissue of a subject, the method including:

placing a distal portion of a pinching device on the tissue, the distal portion of the pinching device defining two or more pinching surfaces;

raising a fold of tissue, by pinching the subject's tissue with the pinching surfaces, by advancing the syringe distally through the pinching device; and penetrating the fold of tissue with the distal tip of the syringe needle.

The present invention will be more fully understood from the following detailed description of embodiments thereof, taken together with the drawings, in which:

BRIEF DESCRIPTION OF THE DRAWINGS

FIGS. 1A-E are schematic illustrations of apparatus including tissue-squeezing surfaces, in accordance with an embodiment of the present invention;

DETAILED DESCRIPTION OF EMBODIMENTS

Figure 1B:
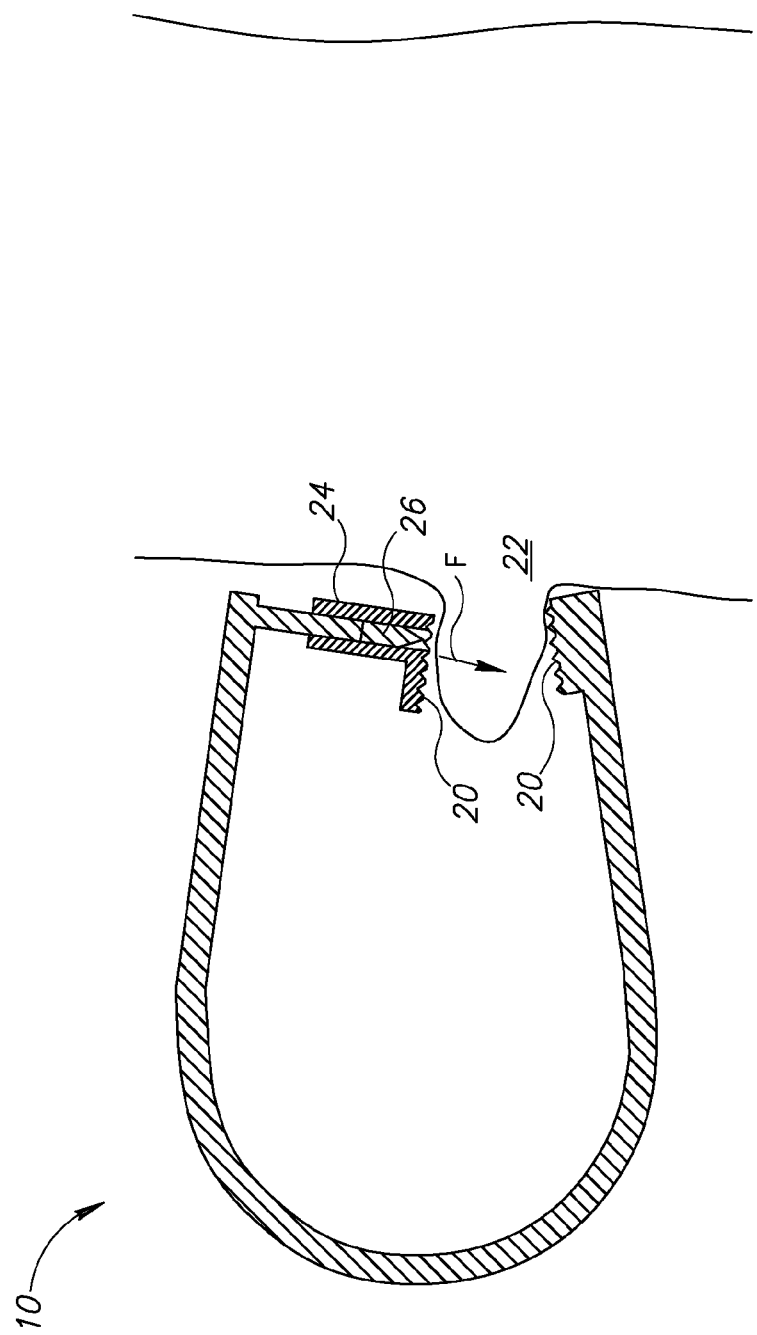
Figure 1C:
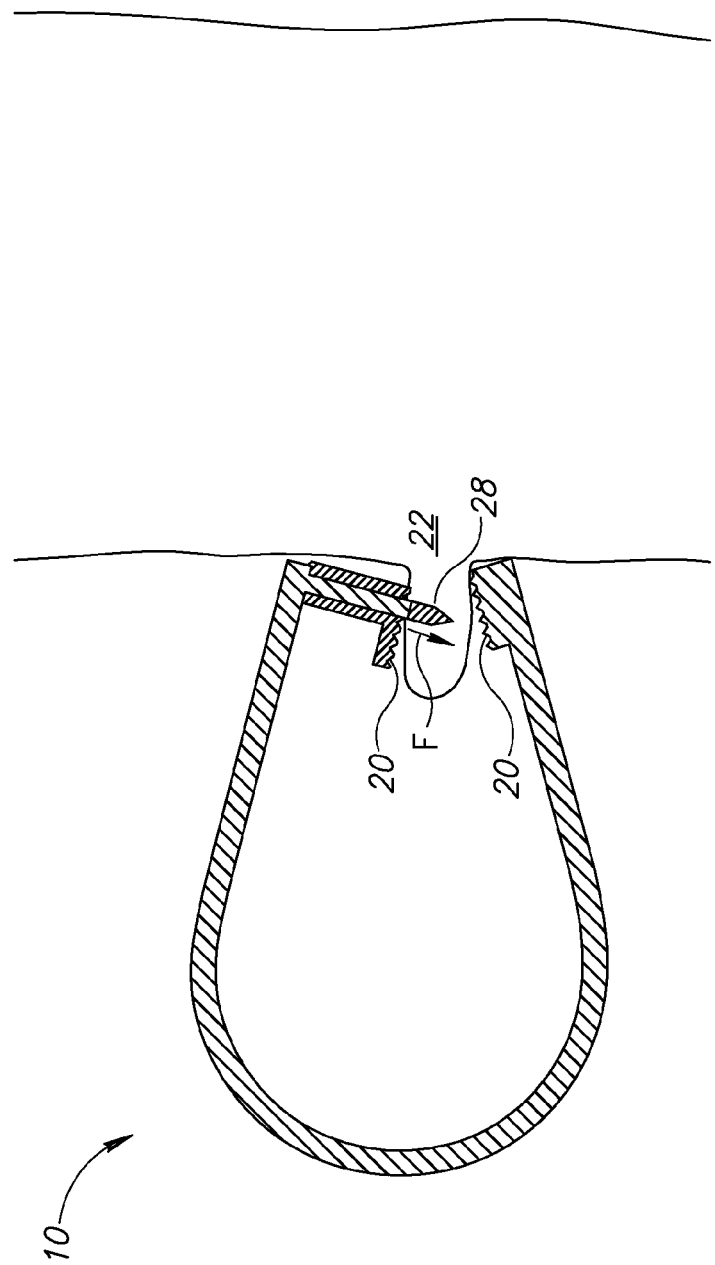

Reference is now made to FIGS. 1A-E, which are schematic illustrations of apparatus 10 including tissue-squeezing surfaces 20 in respective configurations, in accordance with an embodiment of the present invention. In some embodiments, first and second tissue-squeezing surfaces are placed on first and second sides of a subject's tissue 22, for example, the subject's skin, or internal tissue of the subject, such as gastrointestinal tract tissue. A substance 24, for example, a pharmaceutical, is injected into the tissue (as shown in FIG. 1C) by moving the tissue-squeezing surfaces together with a squeezing force F so as to exert pressure on the tissue.

Typically, moving surfaces 20 together causes the substance to move from a first site 26 that is not between the surfaces (i.e., behind one of the squeezing surfaces, as shown in FIG. 1A) to a second site 28 that is between the squeezing surfaces (as shown in FIG. 1C). In some embodiments, the substance is rapidly conveyed from the first site to the second site, when the squeezing surfaces are moved together with a squeezing force F that exceeds a threshold. The threshold force is typically applied with a contact pressure of at least 500 g/cm2, the squeezing force being defined as the force generated between one of the squeezing surfaces and the tissue as schematically illustrated in FIGS. 1A-C).

Figure 1D:
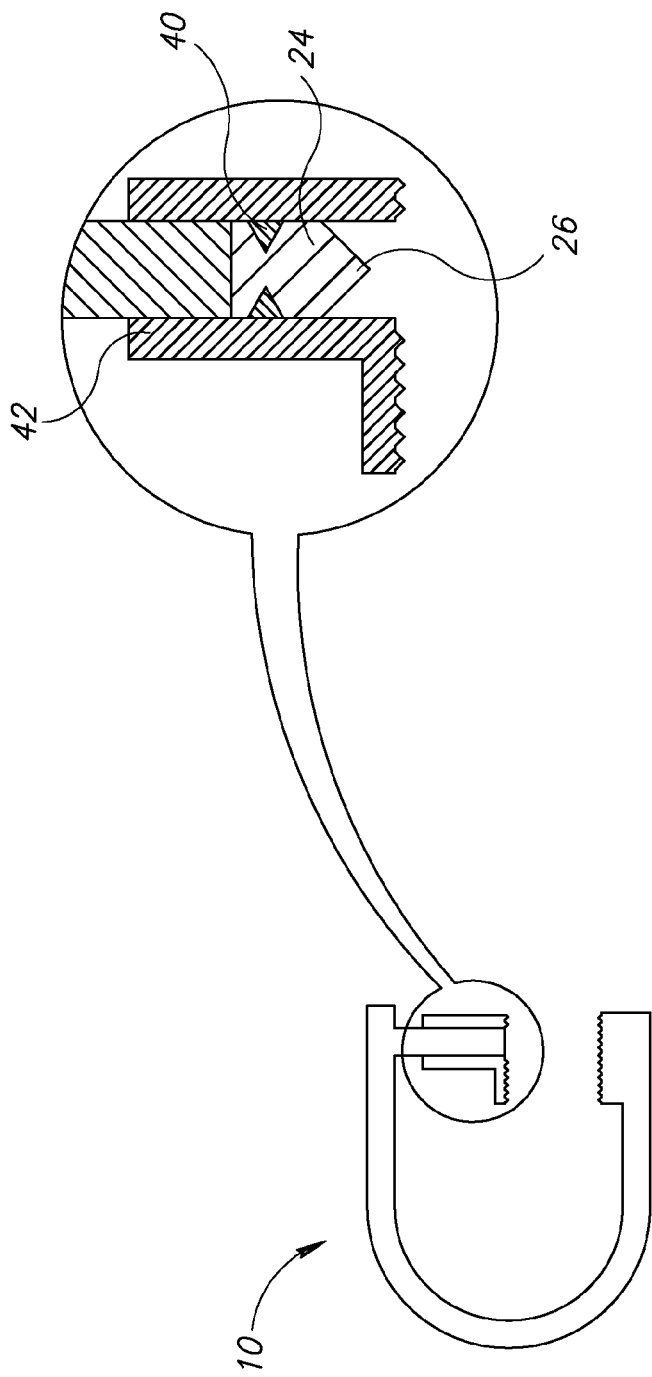

In some embodiments, the substance is a solid mass that is shaped to penetrate the subject's tissue 22 (as shown in FIG. 1D). For some applications, the solid mass is held at first site 26 before the surfaces are moved toward each other. For example, the mass may be held by at least one anchor 40 that is coupled to the squeezing surfaces (e.g., by being coupled to a squeezing surface/anchor interface 42). In the embodiment shown in FIG. 1D, upon application of a supra-threshold squeezing force F to the squeezing surfaces, the anchor breaks off of interface 42, allowing the solid mass to be in injected into tissue 22. For some applications, anchor 40 is a coating on the outer portion of substance 24, which breaks during application of force F.

Figure 1E:
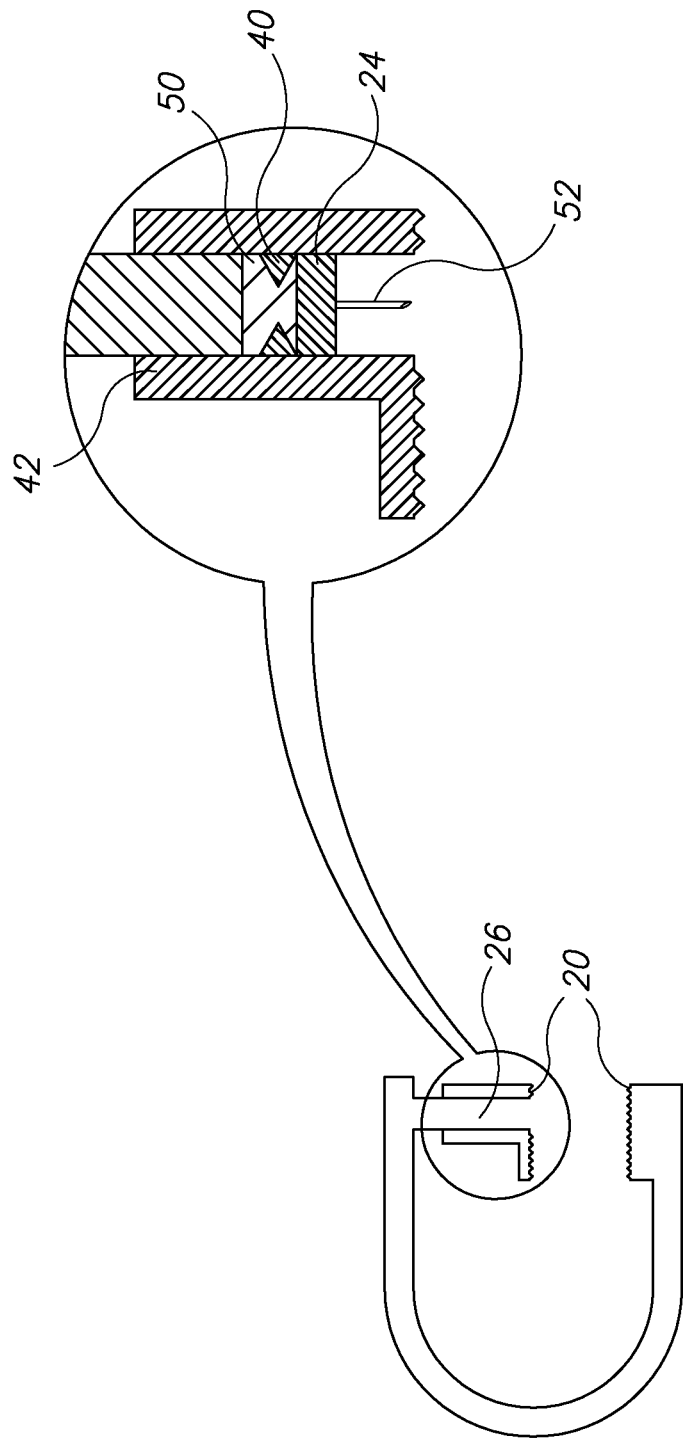

In some embodiments, as shown in FIG. 1E, substance 24 is disposed at first site 26, effectively within a syringe in which interface 42 constitutes the barrel, and a plunger 50 is coupled through substance 24 to a syringe needle 52. Moving squeezing surfaces 20 together causes anchor 40 to decouple from interface 42, allowing syringe needle 52 to penetrate tissue 22, and for plunger 50 to subsequently administer substance 24 through syringe needle 52.

Figure 2:
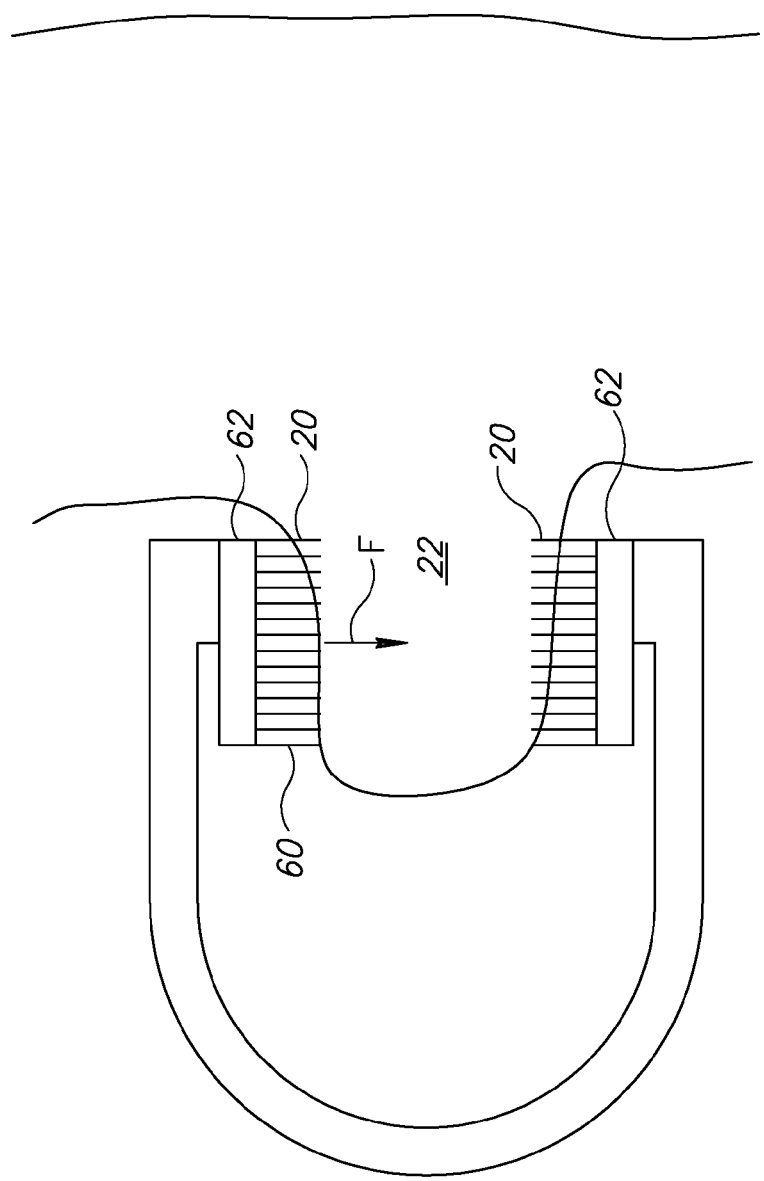
FIG. 2 is a schematic illustration of tissue squeezing surfaces comprising microneedles, in accordance with an embodiment of the present invention.

Reference is now made to FIG. 2, which is a schematic illustration of tissue squeezing surfaces 20 having microneedles 60, in accordance with an embodiment of the present invention. Typically, moving the squeezing surfaces together with squeezing force F causes the microneedles to penetrate the subject's tissue 22. In some embodiments, the substance is disposed on the surface of the microneedles. Alternatively or additionally, prior to moving the squeezing surfaces together, the substance is disposed in a reservoir 62. Subsequent to the microneedles penetrating the tissue, the substance flows from the reservoir into the tissue, via the microneedles. For some applications, reservoir 62 is configured such that application of force F during and/or after penetration of the tissue by the microneedles causes the substance to be released through the microneedles. For example, fluid pressure in toe reservoir may increase during application of force F. In some embodiments, both the first and the second squeezing surfaces have microneedles (as shown). Alternatively, only one of the squeezing surfaces has microneedles.

Figure 3A:
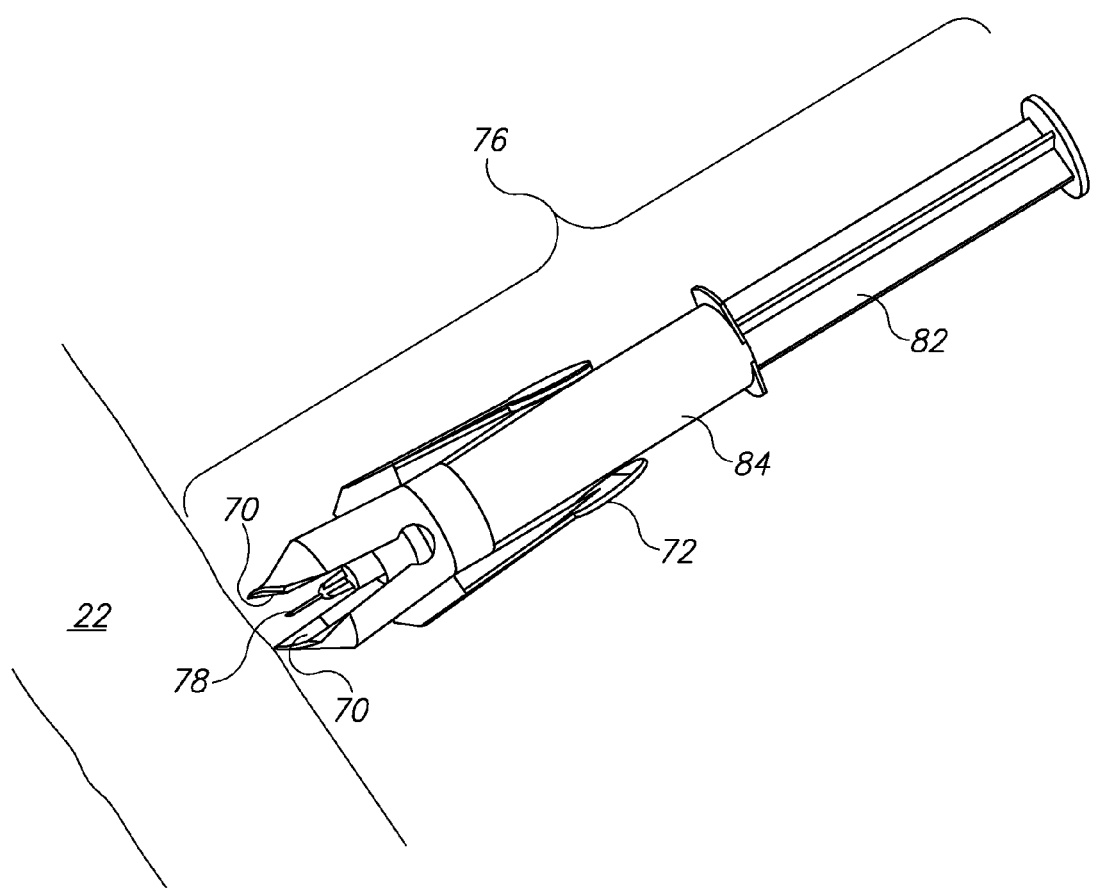
FIGS. 3A-D are schematic illustrations of respective stages of an injection procedure, in accordance with an embodiment of the present invention.

Reference is now made to FIGS. 3A-D, which are schematic illustrations of respective stages of an injection procedure using pinching surfaces 70, in accordance with an embodiment of the present invention. The pinching surfaces are typically coupled to a syringe having a syringe needle 78, the surfaces being disposed distal to the distal tip of the needle. In some embodiments, pinching surfaces 70 are coupled by a user e.g., a physician) to a standard syringe that is typically packaged and purchased separately from the pinching surfaces. Alternatively, the pinching surfaces are manufactured and/or packaged as an integrated device together with the syringe. The injection procedure typically comprises the following steps:

(1) Pinching surfaces 70 are moved away from each other (i.e., opened), using one more operating elements, for example, handles 72, as shown in FIG. 3A.

Figure 3B:
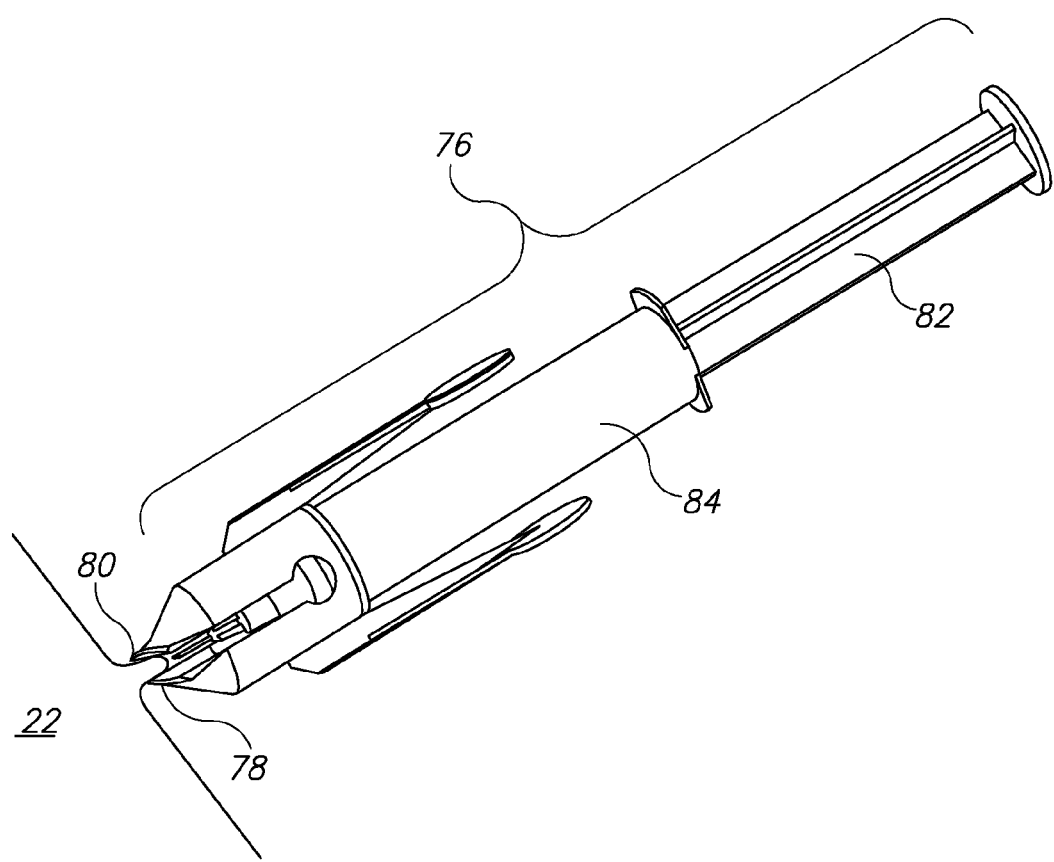

(2) The pinching surfaces are placed against tissue 22 and are moved toward each other (i.e., closed), so as to pinch a fold 80 of the tissue toward the distal tip of syringe needle 78, until the distal tip of the syringe needle is disposed within the fold of tissue. FIG. 3B is a schematic illustration of the syringe needle disposed within the fold of tissue as a result of the pinching surfaces pinching the fold of tissue. Typically, the tissue is pinched with a pinching pressure of at least 200 g/cm2, e.g., 200 g/cm2 to 2000 g/cm2.

Figure 3C:
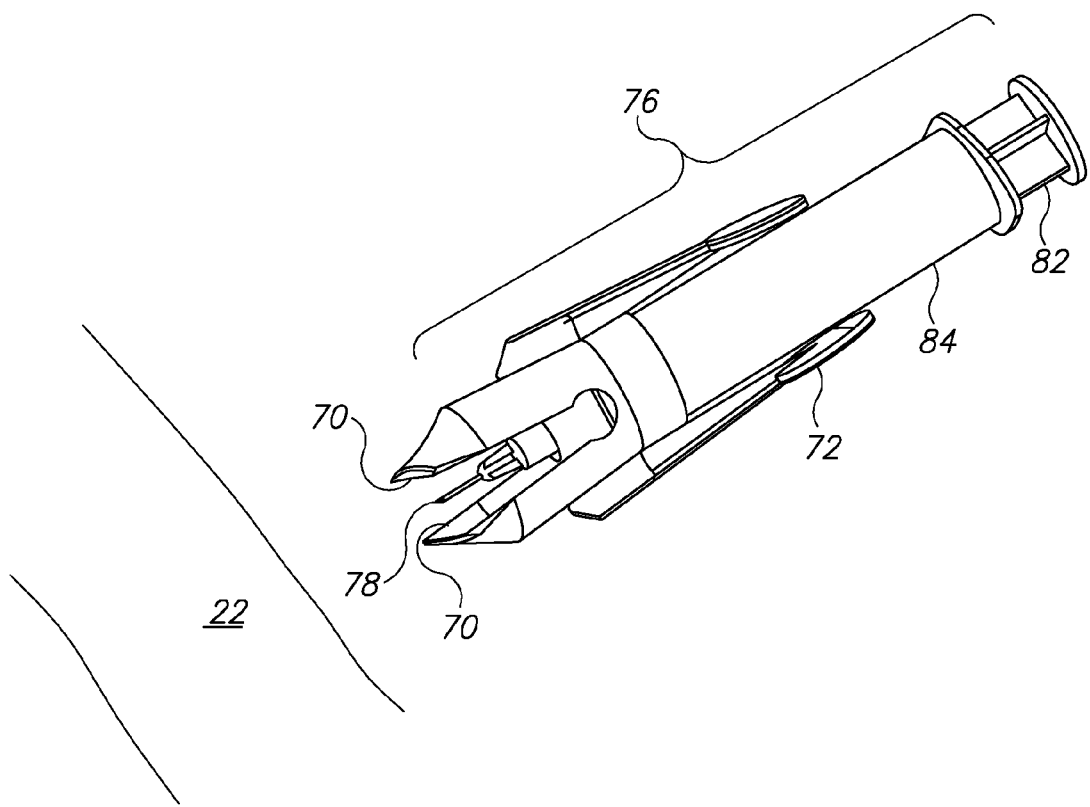

(3) A substance is administered to the subject by advancing syringe plunger 82 through barrel 84 of the syringe. Subsequent to the administration of the substance to the subject, pinching surfaces 70 are opened and removed from the subject's tissue 22, typically by means of handles 72. FIG. 3C is a schematic illustration of the pinching surfaces having been opened and removed from the tissue, subsequent to plunger 82 having been advanced through barrel 84.

Figure 3D:
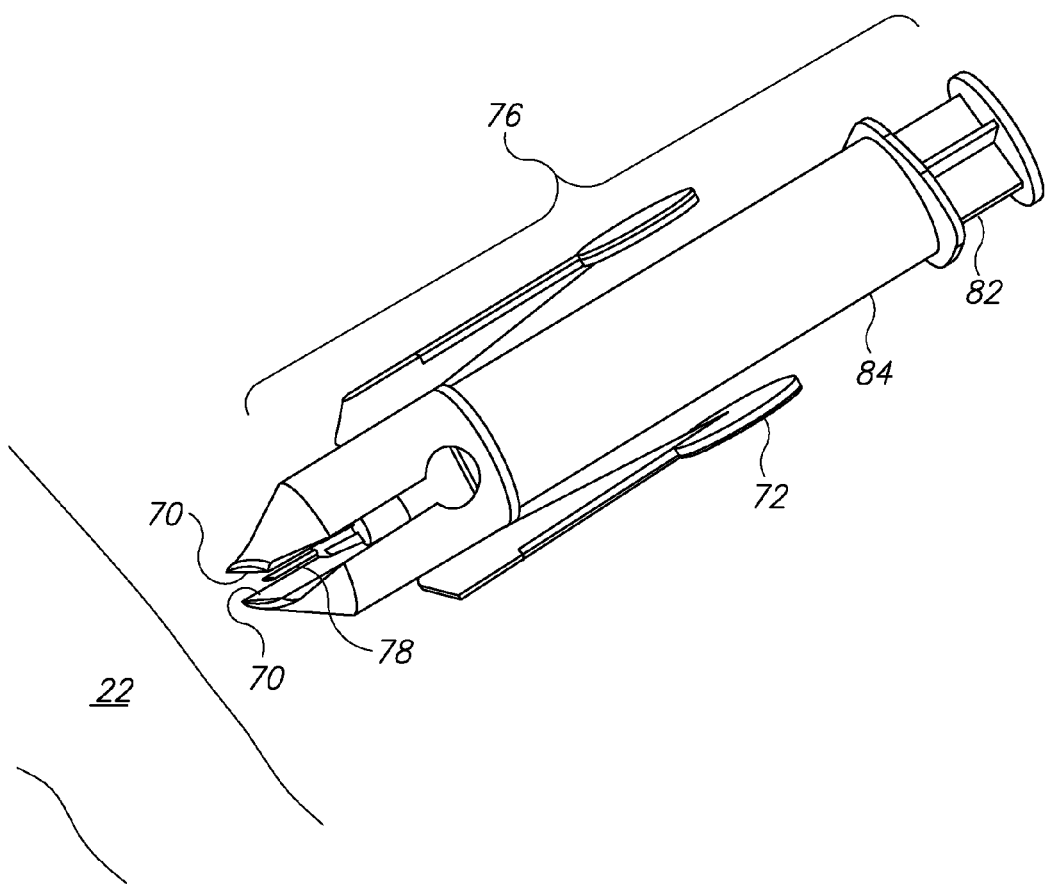

(4) Pinching surfaces 70 are closed so that needle 78 is not exposed. FIG. 3D shows the pinching surfaces covering the needle subsequent to an injection. This closed position of pinching pinching surfaces 70 is typically the "rest" position of the pinching surfaces, if no force is being applied to handles 72.

Figure 4A:
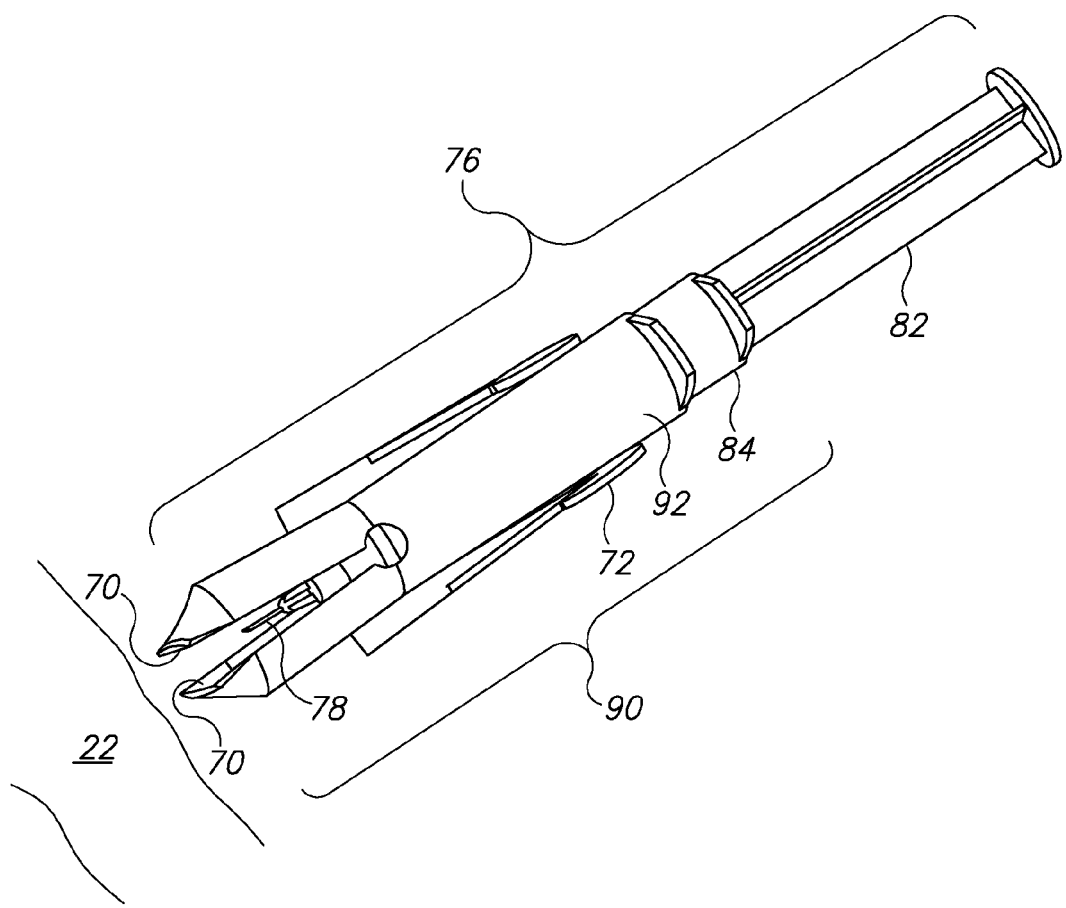
FIGS. 4A-D are schematic illustrations of respective steps of an injection procedure, in accordance with an alternative embodiment of the present invention.

Reference is now made to FIGS. 4A-D, which are schematic illustrations of respective steps of an injection procedure using pinching surfaces 70, in accordance with an alternative embodiment of the present invention. The proximal portion 92 of a pinching device 90 is typically coupled to syringe 76, the distal portion of the pinching device comprising pinching surfaces 70. In come embodiments, the proximal portion of pinching device 90 engages an outer surface of a standard syringe that is typically packaged and purchased separately from the pinching device. For example, pinching device 90 may be shaped to define a lumen, and a standard syringe is inserted by a user (e.g., a physician) into the lumen. In some embodiments, the pinching device is manufactured and/or packaged as an integrated device with syringe 76. An injection procedure using pinching device 90 typically comprises the following steps:

(1) Pinching surfaces 70 are opened, using one or more operating elements, for example, handles 72, as shown in FIG. 4A.

Figure 4B:
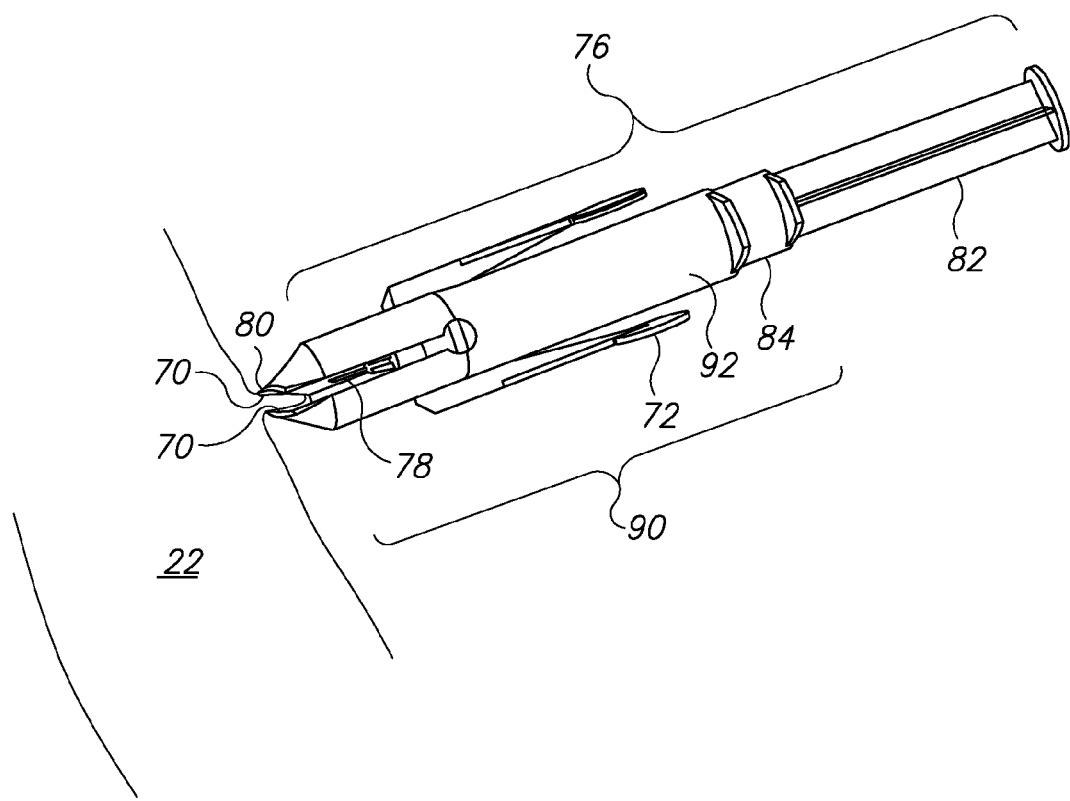

(2) The pinching surfaces are placed against tissue 22 and are moved toward each other so as to pinch a fold 80 of the tissue toward the distal tip of syringe needle 78. FIG. 4B is a schematic illustration of the fold of tissue pinched between squeezing surfaces 70. At the stage shown in FIG. 4A, the needle has not yet penetrated tissue 22. Typically, the tissue is pinched with a pinching pressure of at least 200 g/cm2, e.g., 200 g/cm2 to 2000 g/cm2, or 1000 g/cm2 to 2000 g/cm2. Further typically, the pinching of the tissue reduce pain associated with the penetration of the tissue by the distal tip of the needle, for example, by numbing the tissue.

Figure 4C:
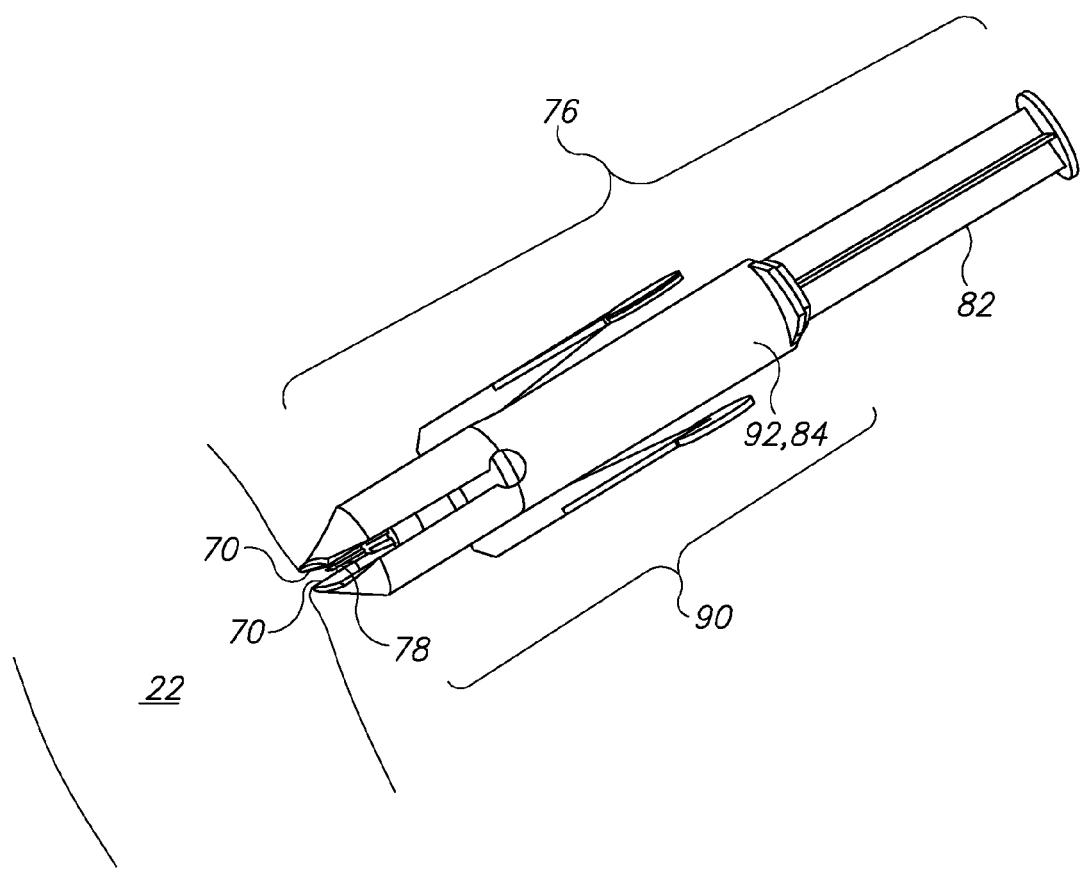

(3) Syringe barrel 84 is advanced distally through pinching device 90, until the distal tip of syringe needle 78 penetrates the subject's tissue, as shown in FIG. 4C.

Figure 4D:
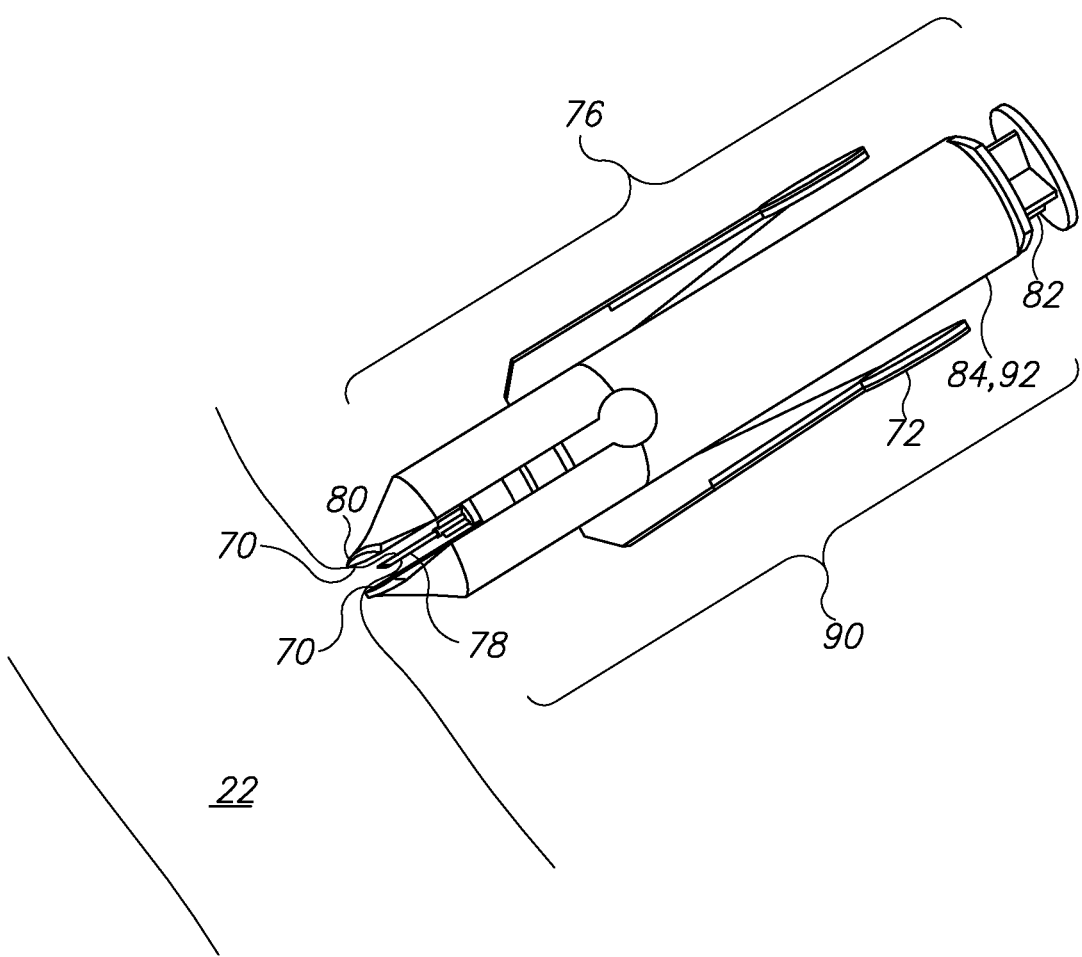

(4) Plunger 82 is advanced distally through barrel 84 in order to administer a substance to the subject, as shown in FIG. 4D.

(5) The pinching surfaces are opened and the device is removed from the tissue. Subsequently the pinching surfaces are closed in order to cover the needle. These steps are generally similar to steps (3) and (4) described hereinabove, with respect to FIGS. 3C and 3D.

Reference is now made to FIGS. 5A-D, which are schematic illustrations of respective steps of an injection procedure using an automatic pinching device 100, in accordance with an embodiment of the present invention. Pinching device 100 comprises pinching surfaces 70 which are configured to pinch a fold of the subject's tissue 22, in response to syringe 76 being advanced distally through the pinching device. Typically, pinching device 100 defines one or more contact surfaces 102, which are contacted by the syringe during the distal advancement of the syringe through the pinching device. One or more helical portions 104 are coupled between the contact surfaces and the pinching surfaces. In some embodiments, device 100 is coupled by a user (e.g., a physician) to a standard syringe that is typically packaged and purchased separately from the pinching surfaces. Alternatively, the pinching device is manufactured and/or packaged as an integrated device together with the syringe. In other aspects, automatic pinching device 100 is generally similar to pinching device 90 described with respect to FIGS. 4A-D.

Figure 5A:
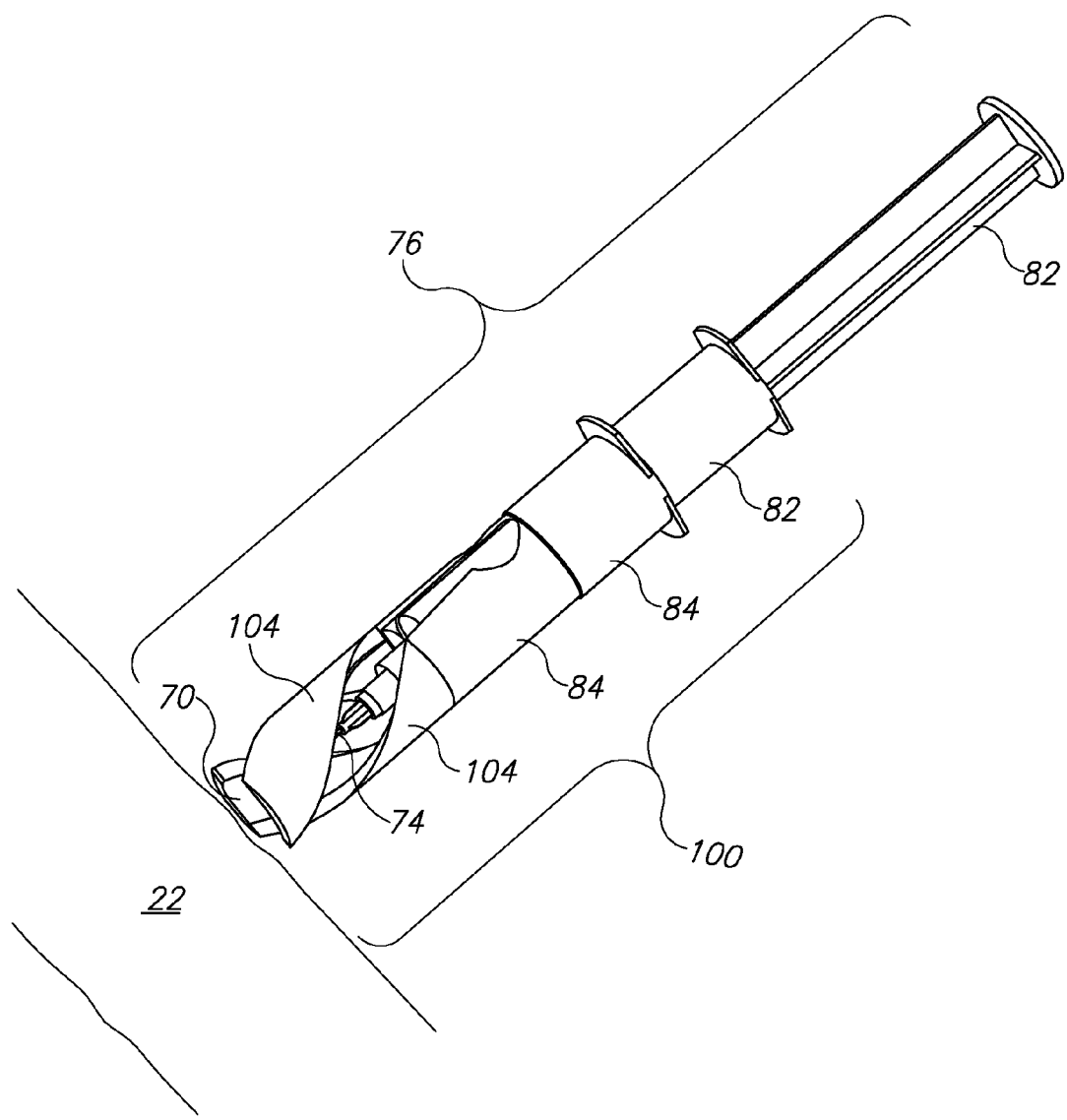
FIGS. 5A-D are schematic illustrations of respective steps of an injection procedure in accordance with a further alternative embodiment of the present invention.

An injection procedure using pinching device 90 typically comprises the following steps:

(1) Pinching surfaces 70 are placed against tissue 22, as shown in FIG. 5A.

Figure 5B:
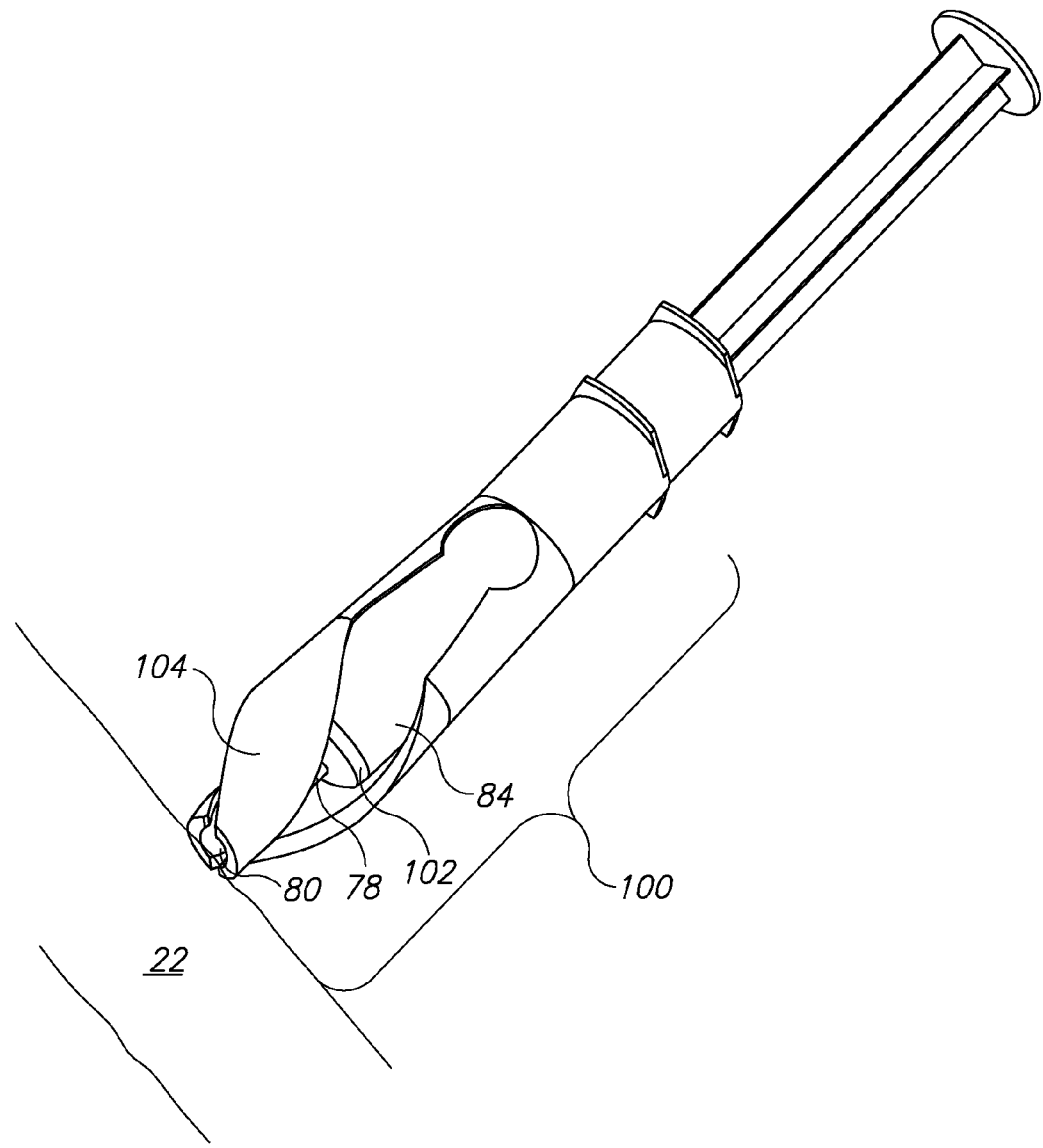

(2) Syringe barrel 84 is advanced distally through pinching device 100. The distal end of the syringe barrel contacts surfaces 102, causing pinching surfaces 70 to pinch a fold 80 of tissue 22 toward syringe needle 78, as shown in FIG. 5B. Typically, the tissue is pinched with a pinching pressure of at least 200 g/cm2, e.g., 200 g/cm2 to 2000 g/cm2.

Figure 5C:
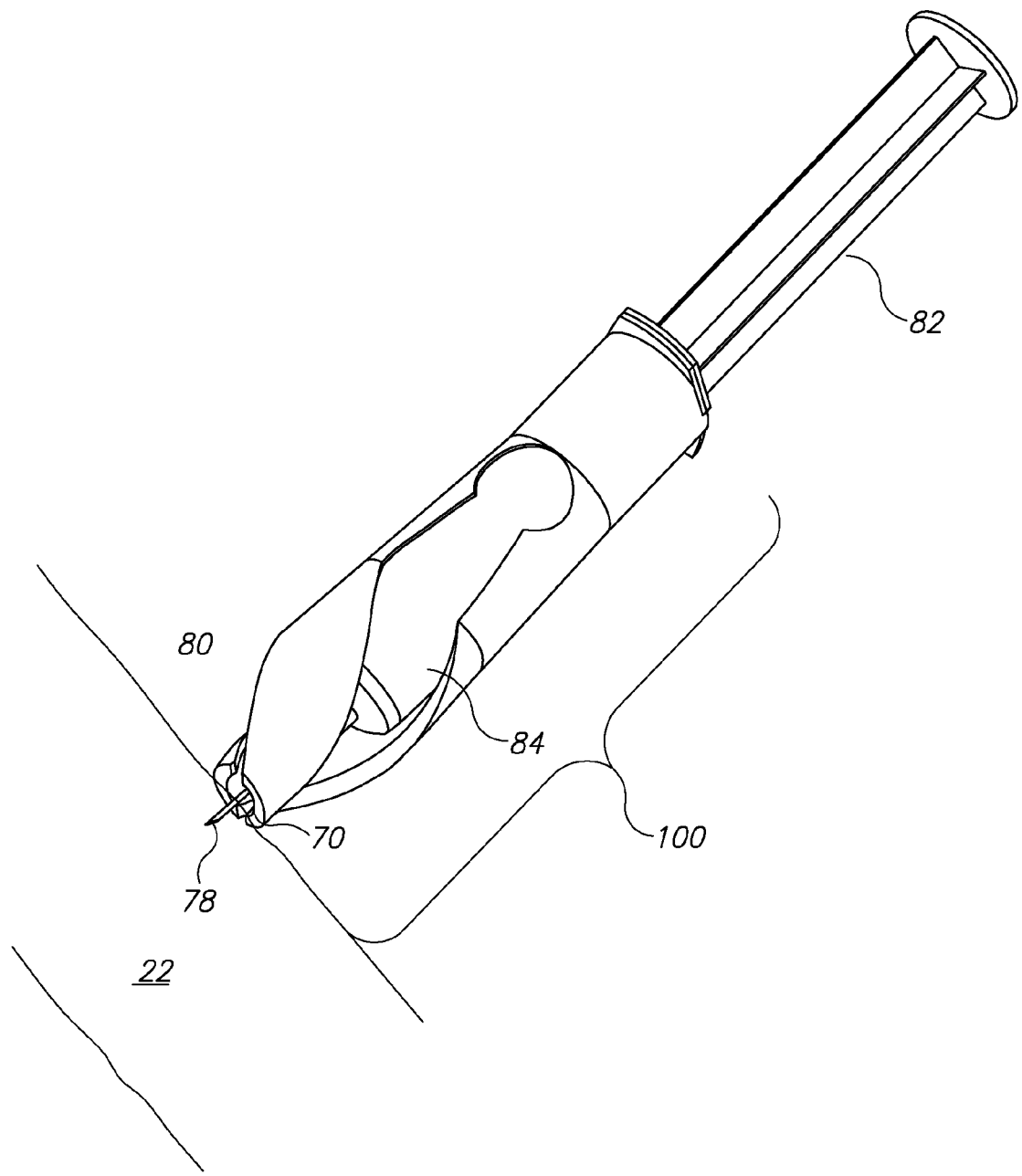

(3) Syringe barrel 84 is further advanced distally through pinching device 100, such that needle 78 penetrates fold 80 of the tissue, as shown in FIG. 5C.

(4) Syringe plunger 82 is advanced distally through syringe barrel 84 in order to administer a substance to the subject. This step is generally similar to step (4) described hereinabove with respect to FIG. 4D.

Figure 5D:
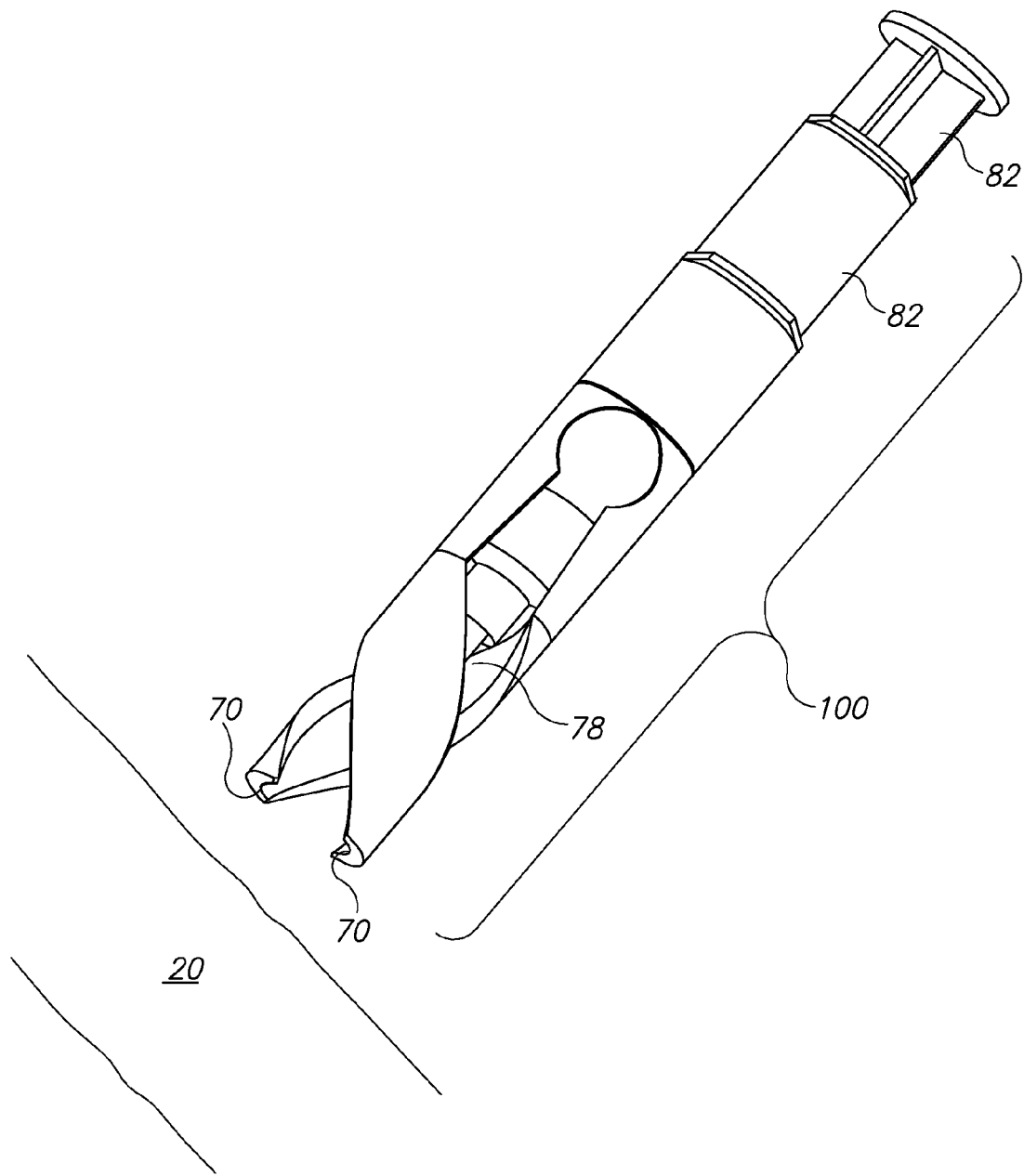

(5) Syringe barrel 84 is withdrawn proximally through pinching device 100. Withdrawing the barrel removes needle 78 from tissue 22, and cases pinching surfaces 70 to move away from each other such that the pinching surfaces no longer pinch the fold of tissue. The pinching device is removed from the subject's tissue and the needle is covered by the pinching device, so that the needle is not exposed, as shown in FIG. 5D.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for use with tissue of a subject, comprising: a substance configured to be injected into the tissue; and first and second tissue-squeezing surfaces configured to be placed on first and second sides of the tissue, the first and second tissue-squeezing surfaces exerting pressure on the tissue by being moved toward each other in response to a squeezing force, the first and second tissue-squeezing surfaces facilitating injection of the substance into the tissue by releasing the substance upon breaking or decoupling an anchor coupled to the tissue-squeezing surfaces in response to application of the squeezing force, wherein the tissue includes skin of the subject, and wherein the tissue-squeezing surfaces comprise skin-squeezing surfaces configured to exert pressure on the subject's skin by being moved toward each other in response to a squeezing force.

2. The apparatus according to claim 1, wherein at least one of the tissue-squeezing surfaces comprises an array of microneedles, the microneedles being configured to exert pressure on the tissue and to penetrate the tissue in response to the application of the squeezing force.

3. The apparatus according to claim 2, wherein the substance is disposed on a surface of the microneedles.

4. The apparatus according to claim 2, further comprising a substance reservoir, wherein when the squeezing force is not applied, the substance is disposed within the substance reservoir, and wherein the substance is configured to be injected into the tissue from the reservoir via the microneedles, in response to the application of the squeezing force.

5. The apparatus according to claim 1, wherein when the squeezing force is not applied, the substance is disposed at a first site that is not between the squeezing surfaces, and wherein the apparatus is configured to convey the substance from the first site to a second site that is between the squeezing surfaces, in response to the application of the squeezing force.

6. The apparatus according to claim 5, further comprising a syringe and a needle coupled thereto, disposed at the first site when the squeezing force is not applied, wherein the substance is disposed within the syringe, and wherein the needle is configured to penetrate the tissue and release the substance into the tissue in response to the application of the squeezing force.

7. The apparatus according to claim 5, wherein the apparatus is configured to rapidly convey the substance to the second site in response to the squeezing force exceeding a threshold.

8. The apparatus according to claim 7, wherein the threshold force is defined as a force generated between one of the squeezing surfaces and the tissue, and wherein the apparatus is configured such that the threshold force is applied at a contact pressure of at least 500 g/cm2.

9. The apparatus according to claim 5, wherein the substance comprises a solid mass, and wherein the solid mass is shaped to penetrate the tissue in response to the application of the squeezing force.

10. The apparatus according to claim 9, wherein the apparatus is configured to hold the solid mass at the first site when the squeezing force is not applied, and to decouple the solid mass from at least one of the squeezing surfaces after injection of the solid mass into the tissue.

11. The apparatus according to claim 1, wherein the squeezing force is applied generally perpendicularly to the first and second sides of the tissue.

12. An apparatus for use with a syringe that has a syringe needle, the apparatus comprising:
pinching surfaces configured to be disposed distal to a distal tip of the syringe needle, and to facilitate penetration of tissue of a subject by the distal tip of the syringe needle, by pinching a fold of tissue toward the distal tip of the syringe needle until the distal tip of the syringe needle is disposed within the fold of tissue; and one or more operating elements configured to operate the pinching surfaces, at least a portion of the operating elements move radially outwardly beyond the syringe when the pinching surfaces pinch the fold of tissue,
wherein the tissue includes internal tissue of the subject, and wherein the pinching surfaces are configured to contact the subject's internal tissue and facilitate penetration of the subject's internal tissue by the distal tip of the syringe needle.

13. The apparatus according to claim 12, wherein the pinching surfaces are configured to pinch the fold of tissue using a pinching pressure of at least 200 g/cm2.

14. The apparatus according to claim 13, wherein the pinching surfaces are configured to pinch the fold of tissue using a pinching pressure of 200 g/cm2 to 2000 g/cm2.

15. An apparatus comprising:
a syringe that comprises:
a syringe needle;
a barrel;
a plunger; and
pinching surfaces disposed distal to a distal tip of the syringe needle, and configured to facilitate penetration of tissue of a subject by the distal tip of the syringe needle, by pinching a fold of tissue toward the distal tip of the syringe needle until the distal tip of the syringe needle is disposed within the fold of tissue; and two operating elements each configured to operate one of the pinching surfaces, each operating element being positioned entirely exterior to the barrel.

* * * * *